United States Patent
Legallais et al.

(10) Patent No.: US 10,119,112 B2
(45) Date of Patent: Nov. 6, 2018

(54) MULTI-REACTOR UNIT FOR DYNAMIC CELL CULTURE

(75) Inventors: Cécile Legallais, Villers Sous Saint Leu (FR); Régis Baudoin, Neuilly Plaisance (FR); Eric Leclerc, Margny les Compiegne (FR); Jean-Matthieu Prot, Compiegne (FR); Patrick Paullier, Thourotte (FR)

(73) Assignees: Universite Technologie De Compiegne—UTC (FR); Centre National de la Recherche Scientifique (CNRS) (FR)

( * ) Notice: Subject to any disclaimer, the term of this patent is extended or adjusted under 35 U.S.C. 154(b) by 805 days.

(21) Appl. No.: 13/582,068

(22) PCT Filed: Mar. 2, 2011

(86) PCT No.: PCT/EP2011/053128
§ 371 (c)(1),
(2), (4) Date: Dec. 7, 2012

(87) PCT Pub. No.: WO2011/107519
PCT Pub. Date: Sep. 9, 2011

(65) Prior Publication Data
US 2013/0084632 A1    Apr. 4, 2013

(30) Foreign Application Priority Data

Mar. 2, 2010  (FR) ...................................... 10 51480
Mar. 2, 2010  (FR) ...................................... 10 51482

(51) Int. Cl.
*C12M 1/34*      (2006.01)
*B01L 3/00*      (2006.01)
(Continued)

(52) U.S. Cl.
CPC ........... *C12M 41/46* (2013.01); *B01L 3/5025* (2013.01); *C12M 23/12* (2013.01); *C12M 23/42* (2013.01);
(Continued)

(58) Field of Classification Search
CPC ............ B01L 3/5025; B01L 3/502715; B01L 3/502761; B01L 9/527; B01L 2200/026;
(Continued)

(56) References Cited

U.S. PATENT DOCUMENTS 4,948,564 A * 8/1990 Root ..................... B01D 61/18
                                                     422/534
5,141,719 A * 8/1992 Fernwood ............. B01D 61/18
                                                     210/323.1
(Continued)

FOREIGN PATENT DOCUMENTS

FR          0954288 A    12/1949
WO      2006097749 A1     9/2006
(Continued)

OTHER PUBLICATIONS

Baudoin Régis: "Développement et caractérisation d'une puce ácellules pour le calibrage d'agents toxiques", Thesis Présentée Pour L 'Obtention Du Grade De Docteur De L 'Utc, XX, XX, [Online] Nov. 27, 2008 (Nov. 27, 2008), pp. 1-61, XP002576413, Extrait de l'Internet: <URL:http://tel.archives-ouvertes.fr/docs/00/34/23/42/PDF/Rapport_THESE_Version_finale.pdf>.
(Continued)

*Primary Examiner* — William H. Beisner
*Assistant Examiner* — Danielle B Henkel
(74) *Attorney, Agent, or Firm* — Lerner, David, Littenberg, Krumholz & Mentlik, LLP

(57) ABSTRACT

The present invention relates to a unit (1) comprising a microsystem (150) and at least one set of interface connec-
(Continued)

tions (16) for the microsystem (150); the microsystem (150) comprising a bottom plate (152) bearing the impression of at least one microstructured dynamic cell culture chamber (15), and a top plate (151), characterized in that the at least one microstructured chamber (15) is fluidically connected at inlet and/or at outlet by a set of connections (16) inserted removably into a hole in the upper plate (151). The present invention also relates to a dynamic cell culture system to this effect.

15 Claims, 12 Drawing Sheets

(51) Int. Cl.
    *C12M 1/32*     (2006.01)
    *C12M 3/00*     (2006.01)
    *B01L 9/00*     (2006.01)

(52) U.S. Cl.
    CPC ........ *C12M 33/06* (2013.01); *B01L 3/502715* (2013.01); *B01L 3/502761* (2013.01); *B01L 9/527* (2013.01); *B01L 2200/026* (2013.01); *B01L 2300/0829* (2013.01); *B01L 2300/0877* (2013.01)

(58) Field of Classification Search
    CPC .... B01L 2300/0877; B01L 2300/0829; C12M 41/46; C12M 23/12; C12M 23/42; C12M 33/06
    See application file for complete search history.

(56) References Cited

U.S. PATENT DOCUMENTS

| | | | |
|---|---|---|---|
| 5,612,188 | A | 3/1997 | Shuler et al. |
| 6,197,575 | B1 * | 3/2001 | Griffith et al. ............. 435/288.4 |
| 7,288,405 | B2 | 10/2007 | Shuler et al. |
| 2002/0053245 | A1 * | 5/2002 | Carl ..................... B01L 3/0279 73/864.14 |
| 2005/0142656 | A1 * | 6/2005 | Li et al. ..................... 435/287.1 |
| 2005/0260745 | A1 * | 11/2005 | Domansky et al. ....... 435/294.1 |
| 2005/0287046 | A1 * | 12/2005 | Burnham ............ B01L 3/50255 422/130 |
| 2006/0110822 | A1 * | 5/2006 | Robbins et al. ........... 435/289.1 |
| 2007/0243523 | A1 * | 10/2007 | Ionescu-Zanetti et al. ...... 435/4 |

FOREIGN PATENT DOCUMENTS

| | | |
|---|---|---|
| WO | 2007008609 A2 | 1/2007 |
| WO | 2009024595 A2 | 2/2009 |
| WO | 2010149567 A2 | 12/2010 |

OTHER PUBLICATIONS

French Preliminary Search Report for Application No. FR1051480 dated Nov. 24, 2010.

International Search Report for Application No. PCT/EP2011/053128 dated Jun. 28, 2012.

* cited by examiner

MULTI-REACTOR UNIT FOR DYNAMIC CELL CULTURE

GENERAL TECHNICAL FIELD

The present invention relates to in-vitro culture of cells.

More precisely, it relates to a multi-bioreactor box for dynamic cellular culture in nutritive medium.

PRIOR ART

Cell cultures today are used as tool for toxicological evaluation of substances.

There are also bioreactors reproducing a favourable environment for development and organisation of cells, close to that of tissue or an animal or human element. Because of these, the reaction of an element vis-à-vis a substance like a xenobiotic, a cosmetic, a drug or more generally any active substance can be provided, and pertinent in-vitro models can be developed.

These models are more and more frequently used in pharmaceutical research since they illustrate a serious alternative to in-vivo models, i.e. animal experimentation, against which there are both economic and ethical pressures at the international level.

Cell culture also represents the basis for the creation of artificial elements capable of being substituted for defective or missing elements, one of the issues of tissue engineering.

Bioreactors comprise at both ends of a microstructured chamber (a culture chamber comprising an upper wall and a lower wall having microstructures) a point of entry for fluid and an outlet point for fluid to allow passage of nutritive fluid necessary for the development of cells. The fluid is therefore in circulation, propelled for example by a pump, what is known as dynamic cellular culture. Such a device has been described in patent application FR0954288.

This precursor bioreactor offers excellent results and enables optimal development of cells, but cannot alone satisfy industrial use. It would be preferable to increase the cell culture surface as much as possible.

One solution for this is to use multi-bioreactors, i.e. parallelised bioreactors. These devices should also have reduced bulk. Various systems for integrated cellular culture have been proposed for this purpose.

The Hµrel® system, described by U.S. Pat. Nos. 5,612, 188 and 7,288,405, comprises four double bioreactors arranged in parallel and attached to a peristaltic pump. A tank is also inserted into the circuit, which serves as reserve for nutritive medium, but also space for sampling of samples.

In fact, samplings are made throughout cellular culture to monitor proper development, and during use of cells for toxicological study purposes: after exposure to a substance to be tested, a series of regular samplings for example determines the metabolic response of the cells to this substance, measures clarity (that is, the capacity of the element to eliminate the substance in a given volume), or observes the reaction kinematics of the cells.

The sampling procedure of the Hµrel® system (in a tank) is long and complex, since it is necessary to halt fluid perfusion to be able to take a sample of medium in the tank. Also, this sampling is done far from the bioreactors, engendering the risk that metabolic markers sought via the samplings see their concentration fall between the bioreactor and the tank, due to adsorption phenomena on the surface of the pipes.

It is also evident that the introduction of bioreactors to the perfusion circuit requires a long and delicate operation in sterile conditions to avoid the formation of bubbles, potentially very harmful for developing cells. The addition of a bubble trap to the circuit is also necessary.

In addition, these bioreactors are between two plates of several centimeters thick which have no sets of connectors. The connection is therefore made via end pieces placed in holes in the plates.

This system ensures sealing, but is problematic during insemination in cells. In fact, human cell strains are extremely expensive, and must be put in place as a precaution. The structure of this device involves inseminating two consecutive bioreactors with the same cells, resulting in redundancies.

In addition, as well as complicating the perfusion network since one of each is required per parallelised bioreactor, any tanks and bubble traps prolong the circuits, and equally increase the internal surface of the pipes. This surface is the seat of adsorption of chemical substances in solution. This adsorption skews toxicology tests, as a xenobiotic injected at the start of the circuit would see its concentration fall, or even fall to zero before finding the cells in culture at the end of the circuit. The risk of a false negative is not negligible.

The Bioflux™ 200 and Bioflux™ 1000 systems, described by patent application US2007/0243523, propose a sealed box using a multi-well plate of adapted commerce. A multi-well plate is a standardised plate comprising numerous wells having the role of small test pieces. This is a tool currently used in laboratories, and available in many models. In this adapted plate, microchannels connecting two wells serve as support for cell growth. Sampling is done in the second well, and this is therefore in-situ sampling close to the culture zone. However, the problems of sampling complexity are even worse than in the Hµrel® system, as the multi-well plate has to be entirely uncovered, and therefore the operation of all reactors arranged in parallel must be halted.

In addition, the Bioflux™ system is much less favourable to cell culture: it disallows recirculating dynamic cellular culture, as perfusion of the culture medium is done by application of overpressure. There are no microstructures, but a single channel between two wells. The adherence and the efficacious surface are very weak and the yield drops. An enormous quantity of cells has to be injected blind to inseminate such a device. Knowing that a dose for inseminating a single microbioreactor, of the order of a million cells, costs several hundred euros, it is essential to improve cellular insemination processes so that a manageable tool can be made from it.

Sampling means from other technological domains have also been proposed, but none delivers full satisfaction.

A first possible system is using a derivation method, at the end of which samples can be taken. But the fluid present in this derivation path stagnates, and will pollute it by way of deposits. It has to be cleaned prior to each sampling if a reliable measurement is needed, and this brings up the problems of the prior art (stoppage and disassembly of the circuit), unless a complete second circuit is put in place to perform cleaning, with all the difficulties and attendant costs.

Another possible system utilises a septum, i.e. a small stopper made of rubber, compressed, closing an orifice in the circuit to be sampled. Septums are especially used in medicine (on the head of catheters, for example). Sampling is done by piercing the stopper with the needle of a syringe, the resulting hole closing over naturally by deformation of the material when the needle is withdrawn. However, a septum must be changed after ten samplings (stoppage and disassembly of the circuit again required). The use of a syringe is also adapted to sample volumes of at least several milliliters, which proves incompatible with conventional circuits of cellular culture, whereof the volume total is generally 2-3 mL. The systems cited above utilise micropipettes allowing samplings of only a few tens of microliters.

Apart from what has been mentioned hereinabove with respect to known systems which can each be associated with particular drawbacks or limitations, it is evident that none of the known systems offers the possibility of easy observation of the cells in culture during operation. In fact, it would be interesting to be able to visually monitor the proliferation of cells over time. This constitutes the principal aim of the invention.

PRESENTATION OF THE INVENTION

Another aim of the present invention, in addition but advantageous, is to resolve the abovementioned difficulties by proposing a device which, via a simple structure, parallelises efficient bioreactors of dynamic cellular culture while giving access to one or more of the following advantages:
  omit tanks or external bubble traps,
  reduce the necessary circuit length,
  enable sampling of culture medium in situ during operation.

Another aim of the invention is to achieve this aim by obtaining a product easier to use, no longer threatening destruction of the cellular medium by a bubble, and in which minute volumes can be sampled at high precision with minimal handling.

Still another aim is to enable controlled, rapid, and more economical cellular insemination.

A first aspect of the invention relates to a box comprising a microstructured chamber of dynamic cellular culture. Three main variants illustrate this aspect. These variants can be employed independently of one another, or in a combination of two (or any number of) variants.

According to a first variant of this first aspect of the invention, the present invention relates to a box comprising a microsystem and at least one set of interface connectors of the microsystem, the microsystem comprising a lower plate bearing the impression of at least one microstructured chamber of dynamic cellular culture, and an upper plate, characterised in that the at least one microstructured chamber is connected fluidically at inlet and/or at outlet by the at least one set of connectors inserted detachably into a hole of the upper plate.

Because of this structure, the microsystem can be easily detached any time, placed under a microscope for observation, then replaced.

According to other advantageous and non-limiting characteristics of this variant:
  the box also comprises at least one well, the microstructured chamber being connected to a well via one of the sets of connectors;
  the bottom of the well is at an altitude higher than any point of the chamber;
  the set of connectors is a connector fixed to a hole at the bottom of the well;
  each microstructured chamber is connected to an inlet well and an outlet well each perfused by a set of connections respectively inlet and outlet;
  the box comprises a lower casing covered by a sealed hood held by gripping means;
  the lower casing comprises the microsystem and a multi-well plate, the well being a well of said multi-well plate;
  the multi-well plate is a disposable plate made of polystyrene;
  the multi-well plate is an autoclavable plate made of polycarbonate;
  the hood comprises sets of male connectors perfusing the well and sets of female inlet connectors;
  the box comprises a male connector and a female connector per inlet well and a male connector and two female connectors per outlet well;
  the microsystem comprises polydimethylsiloxane;
  a membrane insert is arranged in at least one of the wells.

According to a second variant of the first aspect of the invention, the present invention relates to a box comprising at least one well and at least one microstructured chamber of dynamic cellular culture, characterised in that each microstructured chamber is connected to a well at outlet, the box also comprising at least one sampling port terminating in the well and located at an altitude higher than any point of this well.

Because of this structure, sampling is completed quite simply by opening the port and inserting therein for example a micropipette directly in the outlet well of the microstructured chamber to be sampled, that is, in the immediate proximity of the cells.

According to other advantageous and non-limiting characteristics of this variant:
  the sampling port is provided with a removable stopper;
  the box comprises a lower casing covered by a sealed hood held by gripping means;
  the sampling port is constituted at inlet by a female connector included in the hood;
  the hood also comprises at least one male connector perfusing the well and being aligned with the female connector;
  each microstructured chamber is connected to an inlet well and an outlet well, each well being perfused by a male connector;
  the hood comprises a female connector by inlet well and a second female connector per outlet well;
  the female connectors of a well are connected to the same male connector perfusing said well, the connector being inclined relative to the alignment formed by said male connector and the female connector;
  the lower casing comprises a multi-well plate, the well being a well of said multi-well plate;
  the lower casing also comprises a microsystem, the wells to which a microstructured chamber is connected being provided on their bottom with holes in which are inserted at least one set of interface connectors of said microsystem;
  the microsystem comprises a lower plate comprising the impression of said at least one microstructured chamber, and an upper plate comprising the set or the sets of connectors;
  the microsystem comprises a lower plate comprising the impression of said at least one microstructured chamber, and an upper plate, the set or the sets of connectors being connectors fixed to the holes perfusing the chamber or the chambers through the holes of the upper plate;
  the microsystem is constituted by polydimethylsiloxane;
  the multi-well plate is a disposable plate made of polystyrene;

the multi-well plate is an autoclavable plate made of polycarbonate;

a probe is placed in at least one of the sampling ports;

said probe is integrated into the stopper of the port;

a membrane insert is arranged in at least one of the wells.

According to a third variant of the first aspect the present invention also relates to a box comprising at least one well and at least one microstructured chamber of dynamic cellular culture, characterised in that each microstructured chamber is connected to a well at inlet, the bottom of the well being at an altitude higher than any point of the chamber.

Because of this structure, the well or wells fulfil the function of bubble trap. Since the column of fluid is located at a higher altitude than the microchambers and each well is perfused from above, the bubbles optionally removed escape upwards by buoyancy. Air cannot be entrained in the circuit.

The wells also fulfil the function of a tank. In fact, the volume of each well is of the order of a milliliter. Connecting each chamber ideally to two wells approaches the classic volume of 2-3 mL in the circuit, and an external tank ceases to be useful.

In addition, this automatic degassing makes the filling procedure of the circuit at the start of culture easier: it is no longer necessary to carefully purge the whole circuit, since during the first rotation of fluid the bubbles escape upstream of the microchamber, so it is enough merely to check that the level of fluid in the first well is sufficient. Over an hour of work is saved. And there is no further risk that the culture is destroyed if this work had not been carried out perfectly prior to insemination.

Finally, these wells enable insemination directly in the chamber without any loss and with need for just one pipette. The operation is therefore rapid, precise, and can be performed on numerous chambers consecutively. There is no further need to use a syringe as in devices of the prior art. The device is operational in a few minutes for minimal cost.

According to other advantageous and non-limiting characteristics of this variant:
- each microstructured chamber is connected directly to a well via a hole at the bottom of the well;
- the box comprises a microsystem, sets of interface connectors of said microsystem being inserted into the hole or holes;
- the microsystem comprises a lower plate comprising the impression of said at least one microstructured chamber, and an upper plate;
- the set of connectors is a deformable tube forming part of said upper plate, via which the point of an insemination pipette can be inserted into the chamber;
- the set of connectors is a connector fixed to the hole perfusing the chamber through holes of the upper plate;
- each microstructured chamber is connected to an inlet well and an outlet well each perfused by a set of connections respectively inlet and outlet;
- the box comprises a lower casing covered by a sealed hood held by gripping means;
- the lower casing comprises the microsystem and a multi-well plate, the well being wells of said multi-well plate;
- the hood comprises sets of male connectors perfusing the well and sets of female inlet connectors;
- the box comprises a male connector and a female connector per inlet well and a male connector and two female connectors per outlet well;
- the microsystem is constituted by polydimethylsiloxane;
- the multi-well plate is a disposable plate made of polystyrene;
- the multi-well plate is an autoclavable plate made of polycarbonate;
- a membrane insert is arranged in at least one of the wells.

According to a second aspect of the invention the invention also proposes a dynamic cellular culture system, characterised in that it comprises:
- a box according to one of the variants (or combination of variants) of the first aspect of the invention, and
- at least one fluid circuit comprising circulation piping fitted with circulation means and connected to at least one microstructured chamber.

According to other advantageous and non-limiting characteristics of this system:
- the circulation means are a multichannel peristaltic pump.

Because of the omission of bubble traps and tanks, it is possible to reduce the length of the perfusion circuit by half. The results of toxicological studies on a cellular culture system according to the second aspect of the invention will be all the more reliable vis-à-vis similar tests performed on known devices.

According to a third aspect, the invention finally proposes a method for cellular insemination of a box according to one of the variants (or combination of variants) of the first aspect of the invention, characterised in that it comprises the steps of:
a) Opening the hood;
b) Introduction of cells to be inseminated to a pipette;
c) Insertion of the point of the pipette into a set of connections;
d) Injection of cells directly into the microstructured chamber from the pipette;
e) Tight closing of the hood and locking by gripping means.

According to other advantageous and non-limiting characteristics of this method:
- the pipette is a gauged micropipette, calibrated to contain a predetermined quantity of cells corresponding to optimal insemination of a microstructured chamber;
- steps b), c) and d) are repeated as many times as there are chambers in the microsystem;
- the pipette is a multichannel gauged pipette adapted to the multi-well plate.

PRESENTATION OF FIGURES

Other characteristics and advantages of the present invention will emerge from the following description of a preferred embodiment. This description will be given in reference to the attached diagrams in which:

FIG. 2a shows fluid sampling, FIG. 2b discloses the fluid path into the box, and FIG. 2c shows cellular insemination of a microstructured chamber;

DETAILED DESCRIPTION

General Architecture

The box 1 according to the invention preferably specifies parallelisation of the bioreactors. In some embodiments it will be designated as a multi-reactor box. However, the invention is not limited to this embodiment and can comprise one microstructured chamber 15 only.

Figure 1:
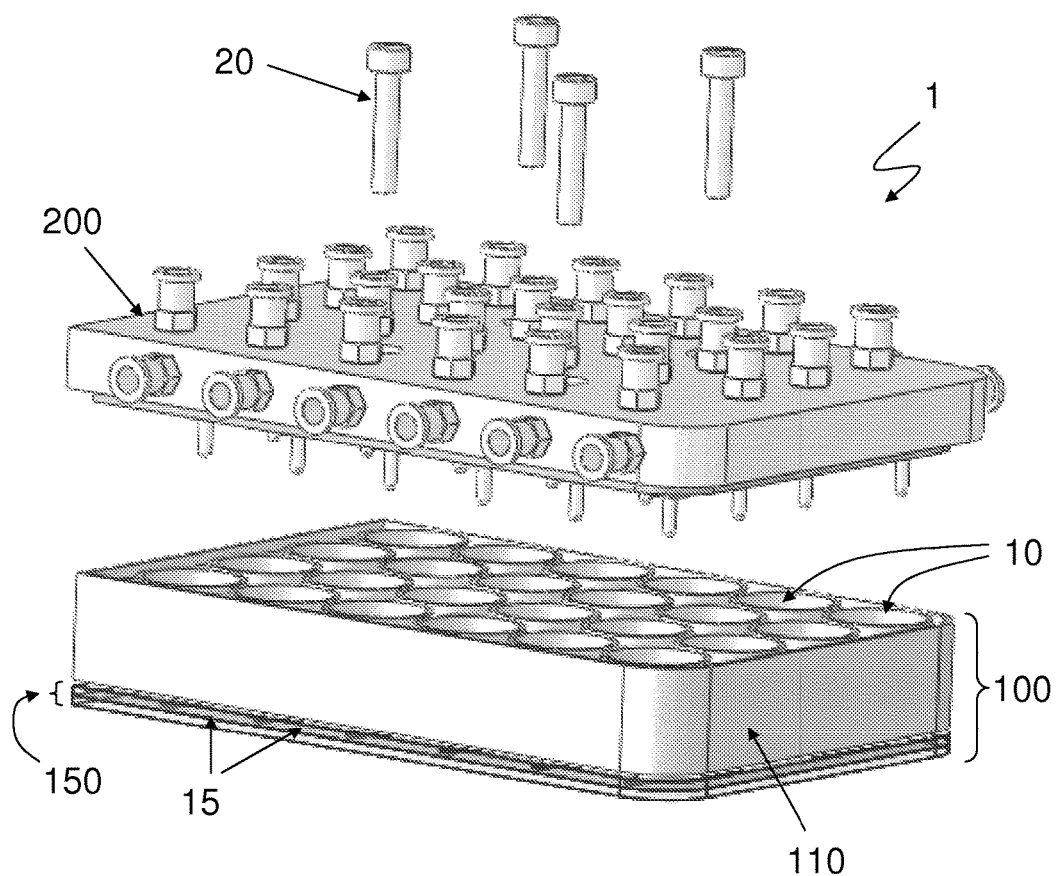
FIG. 1 is an exploded perspective view of a box according to the invention.

In the embodiment preferred illustrated by the figures, the box 1 comprises a lower casing 100 covered by a sealed hood 200 held by a clamping system 20, for example four screws passing through it, as illustrated in FIG. 1.

Figure 4:
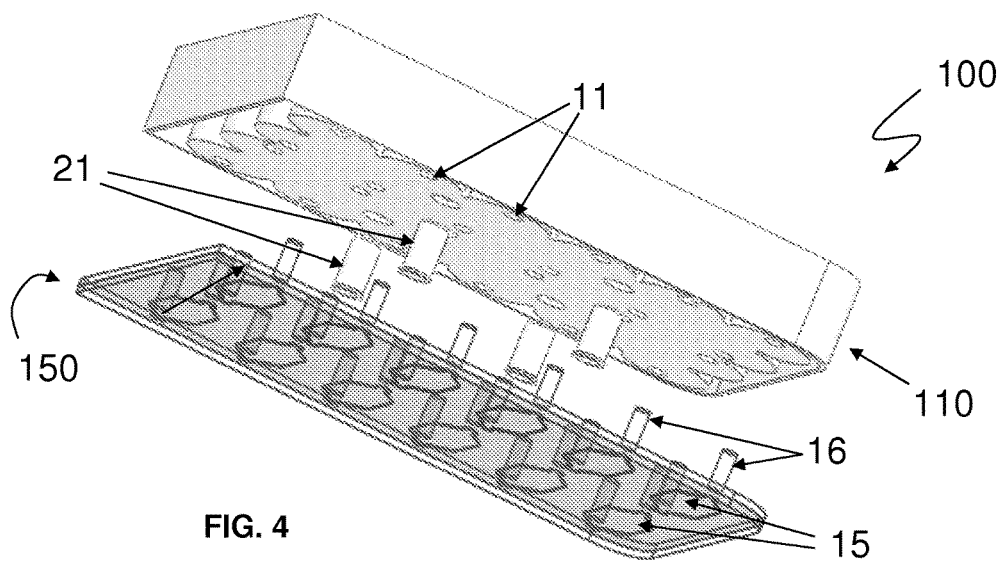
FIG. 4 is an exploded perspective view of the lower casing of the box according to the invention.

This casing 100, more clearly seen in detail in FIG. 4, comprises a multi-well plate 110, including the well or wells 10, and a microsystem 150. Threaded spacers 21 can be arranged between the well 10 to complement the gripping means 20. These spacers 21 can be an integral part of some multi-well plates 110, or be tubes inserted into orifices pierced in the casing, and glued in.

Figure 2A:
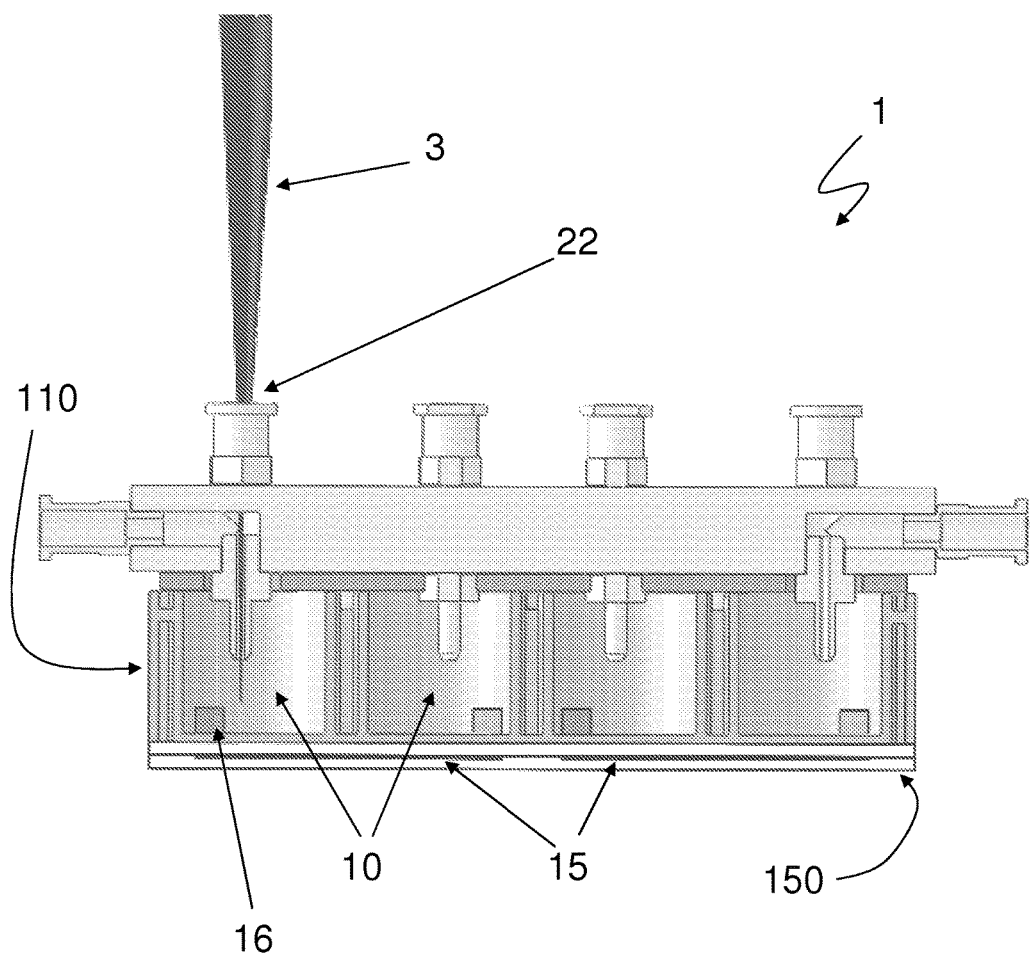
FIGS. 2a, 2b and 2c are three transversal sections of the box according to the invention, uncovered in 2c.
Figure 2B:
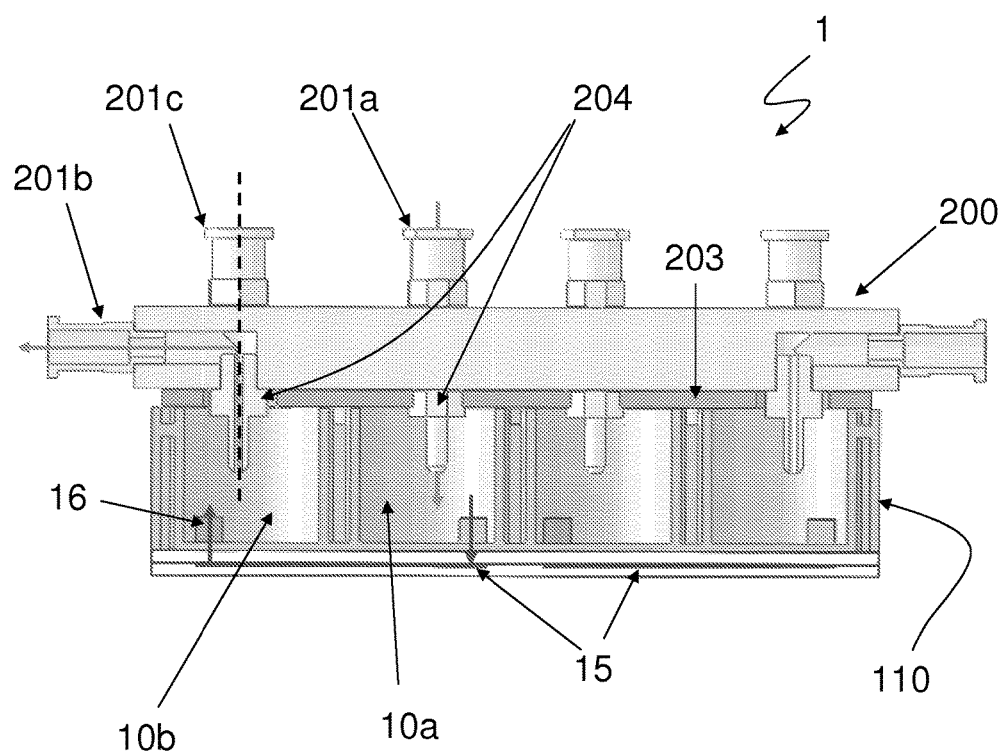

The multi-well plate 110 is an item well known to the person skilled in the art, which can be in numerous forms and which is sometimes called microtitre plate, in reference to small calibrated volumes of the wells. Conventionally, these are arranged according to a matrix in a 2:3 ratio, and plates of 6, 12, 24, 96 or 384 wells are generally commercially available. Advantageously, for considerations associated with the volume of the wells, the multi-well plate 110 according to the invention is a 24-well plate. Such a box contains six rows of four wells 10 arranged as shown in FIG. 2a or 2b. In this architecture, the central wells are inlet wells 10a, and the two lateral wells are outlet wells 10b.

At the bottom the wells 10 are pierced by holes 11 which effect communication of fluid between the well 10 and the microstructured chambers 15. Each hole 11 inseminates efficiently, since the cell strains injected into this hole fall into the microstructured chamber 15 to which it is connected. There is no dead volume in which the cells would be deposited before reaching the chamber, as in the prior art.

Fluid Sampling

FIG. 2a illustrates the box in a variant, which can be used alone or combined with one or more other variants in a fluid sampling situation. The point of a sampling pipette 3 is inserted into a port 22. This port 22 is located at an altitude higher than any point of the well 10 below it. Higher altitude means conditions such that any drop of fluid from the well 10 has less potential gravity energy than a drop which would pass through the port 22. This is the case when placing the box 1 according to the invention in a normal operating position, that is, with the bottom of the lower casing 100 placed on a surface close to the horizontal.

This structure allows fluid samplings from the well 10 without perfusion having to be stopped, as compared to what has been offered to date.

Figure 3A:
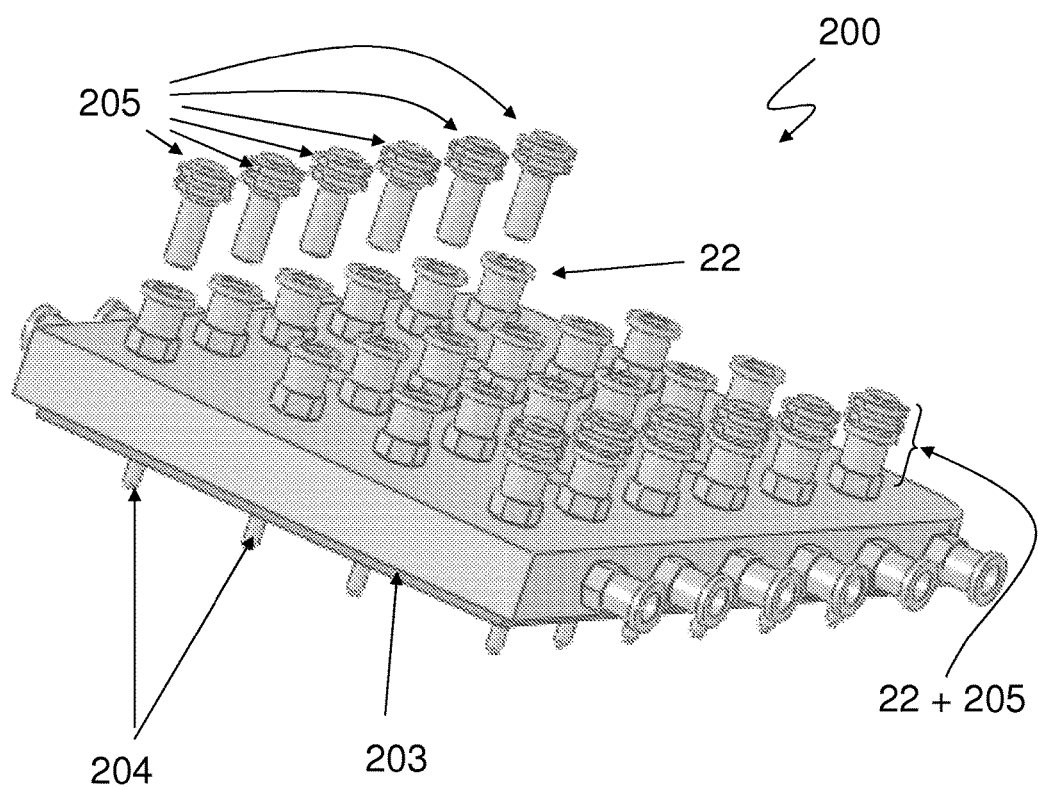
FIG. 3a is a perspective view of the hood of the box according to the invention in which a possible system for closing the sampling ports is shown.

In fact, the port 22 is closed under normal operating conditions. For this, it comprises a stopper 205, or any other equivalent device making it easy to open and close the port 22. FIG. 3a shows an example. Due to the difference in altitude between the port 22 and the well 10 there is no fluid immediately under the stopper 205, but some air is trapped. This means that when the port 22 is opened for sampling, there is no immediate risk of fluid spillover, or any problem of fluid stagnating and polluting the port 22.

Sampling is performed by opening the stopper 205 of the port 22, quickly introducing the point of the sampling pipette 3 into the well 10 and drawing up a required volume before withdrawing the pipette 3 and reclosing. The well 10 equipped with the port 22 is an outlet well 10b, in other words it receives the fluid just after it has entered the microstructured chamber 15 to which this well 10b is connected.

Advantageously, the port 22 passes through the sealed hood 200 so as to allow sampling without the box 1 having to be uncovered, as is often the case for known systems.

Structure of the Hood

It is pointed out that the sealed hood 200 is an optional element of the invention which can be the object of numerous embodiments.

Figure 3B:
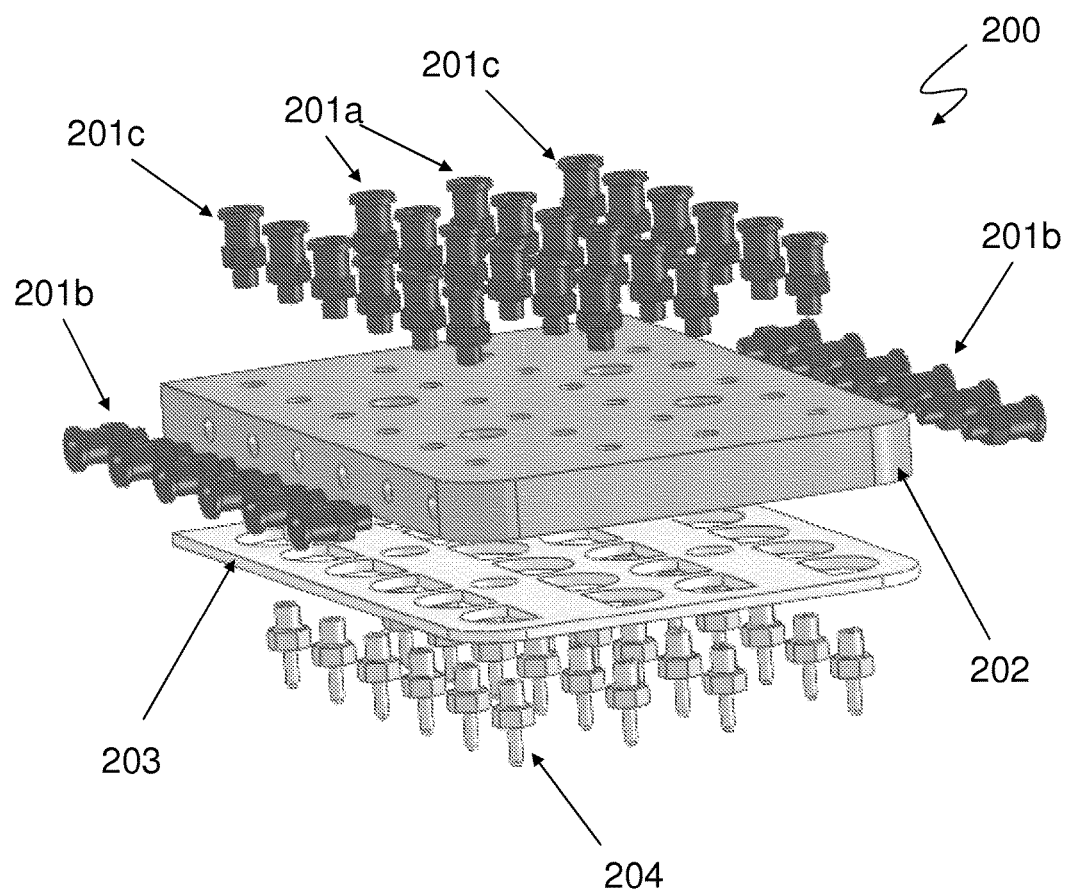
FIG. 3b is an exploded perspective view of the hood of the box according to the invention.

An advantageous hood 200, detailed in FIG. 3b, preferably comprises a plate made of Polycarbonate 10 mm thick into which 24 male connectors made of Polypropylene 204 and 36 female connectors made of Polypropylene 201 are screwed (Ø4 mm 10-32 UNF). Twenty-four of these female connectors 201a and 201c are located on the top of the hood 200, and are aligned with the male connectors 201. The twelve other 201b are on the flank of the hood 200. So when the box is reclosed, and with sealing ensured by a flat PDMS 203 joint 2 mm thick, there is a male connector 204 and one or two female connectors 201 per well 10:

for the inlet well 10a, there is a single connector of each type (201a and 204). The fluid intake is on the top of the hood 200.

for the outlet well 10b there are the two female connectors 201b-c. Only the lateral connector 201b serves as passage for fluid. The female connector 201c constitutes the inlet of the port 22.

As is evident in FIGS. 2a and 2b the female connector 201c and its male connector 204 are aligned. This is what enables insertion of the point of a sampling pipette 3 through these two connectors at the same time, and therefore through the whole hood 200.

Circulation of Fluid in the Lower Casing—Integrated Debubbler System

FIG. 2b shows the fluid path in an advantageous variant of the box 1 which comprises the hood 200 described previously. The fluid penetrates via the female connector 201a and is transmitted to the inlet well 10a via a male connector 204. The fluid contained in this inlet well 10a is then perfused by a set of inlet connections 16 of the microstructured chamber 15 to be collected in the outlet well 10b via a set of outlet connections 16 of the chamber 15. The excess fluid contained in the outlet well 10b is then drawn up by a male connector 204 and conveyed to the female connector 201b of the hood. By paying attention to the volume used it is possible to continuously perfuse the culture chamber. It is pointed out that "perfusing" an element of the box 1, irrespective of whether these are wells 10 or a microstructured chamber 15, means connecting it fluidically, irrespective of whether this is for feeding it with fluid or for evacuating an overflow of fluid. The fluid circulation rates are in fact very low, and the pertinent fluidic communication can be assimilated drop by drop through the different sets of connectors and connectors of the box 1.

It can be noted that the fluid path forms a bend before the female connector 201b. This non-limiting architecture has the two independent outlets 201b and 201c for a single male connector 204. This is construction gimmick by which there can be a specific sampling port 22, always available and capable of receiving a micropipette 3, without complicating the fluid circuit.

In this case, a bifurcation appears inside the hood 200. If the vertical axis of the male connector 204 is followed as it exits from the well 10b, the female connector 201c is traversed with the exit via the sampling port 22, and if the bifurcation is followed the exit is onto the flank of the hood via the female connector 201b.

In addition, since each well 10 has a volume of the order of a milliliter (mL), the two wells 10a-b per chamber 15 are therefore equivalent to an external tank of 3 mL. Also, as is evident from FIG. 2b, any point of the well 10a is located advantageously at an altitude higher than a point of the chamber. Higher altitude here means conditions such that any drop of fluid from the chamber 15 has less potential gravitational energy than any drop from the well 10a. This is the case with placing the box 1 according to the invention in a normal operating position, that is, with the bottom of the lower casing 100 set on a surface close to the horizontal.

Because of this difference in altitude, even if an air bubble were to exit from the connector 204, buoyancy would take it to the top of the well 10a. It would be contrary to mechanics were it to reach the bottom of the well and enter the chamber 15. As already explained, because of this structure it is therefore possible to automatically debubble the circuit provided care is taken with the volume of fluid in the well 10a.

This is also valid during initial filling of the circuit, during which it was necessary to purge the pipes of any air bubble for devices of prior art, as a precaution. In an advantageous variant of the box according to the invention, a variant which can be used alone or combined with one or more other variants, there is direct communication between the well 10 and the chamber 15 via the set of connectors 16. Once the latter has been inseminated and therefore filled by an operator, it suffices to fill each well 10 with nutritive liquid to ensure that there is no air bubble enclosed in the lower casing 100, by simple gravity. The hood 200 is reclosed, and the air bubbles optionally present in the rest of the circuit will be captured by the well 10a. Tests have been conducted and it appears that an operator needs only seven minutes to perfuse a complete multi-reactor box after insemination, that is, twelve bioreactors. This operation used to take between an hour and an hour and a half, during which time the operator had to carefully inject fluid into each bioreactor by means of a syringe, slowly fill the perfusion circuit, then degas it, all of which no longer is needed.

Drawn Samples

In addition to sampling mechanisms described previously, it can also be feasible to carry out samplings in parallel upstream of the chambers 15, especially in the inlet well 10a, for example by installing another port 22 similar to that of the outlet wells 10b. In comparing these new samplings to the outlet samplings, especially by subtracting the inlet magnitudes from the outlet magnitudes, differential measurement of the cellular reaction can be taken. No known system allows this, as it allows for sampling in a single spot only, which is the tank.

In yet another more advanced embodiment, manual sampling by pipette by automatic monitoring via probes can be replaced. In fact, physico-chemical miniaturised probes exist which can be introduced into the sampling ports 22 during all or part of the cellular culture. Monitoring is therefore continuous.

These probes generally comprise a sensor, often piezoresistive, connected by a wire to a measuring instrument which deducts a physical magnitude from the data transmitted by the sensor. Non-exhaustive examples are pH meters, thermometers, conductimeters, flowmeters, manometers, nephelometers or turbimeters, the sensor of which is placed in at least one well 10b, the wire exiting via the port 22 closed off by material ensuring sealing. The sensor can also be the end of one or more fibre optics, registering the emission and/or absorbance range of the fluid being conveyed to a spectrophotometer, because of which the concentration of one or more substances present in solution is calculated permanently.

Advantageously, the probe is integrated into the stopper 205. Because of this, sealing is directly ensured throughout operation of the probe, and it is possible to remove the probe to conduct sampling.

The possibility of one or more probes incorporated in the box according to the invention is no longer pas incompatible with the possibility of differential measurements: automatic measuring at inlet can be compared to automatic measuring at outlet.

It is evident nevertheless that the invention is not limited to any of these embodiments.

Structure of the Microsystem

The microsystem 150 mentioned above is a structure optionally housing the microstructured chamber or microstructured chambers 15 and placed under the multi-well plate 110. It shall be noted that the microsystem 150 can be composed of several distinct elements which can be handled separately. Each element comprises one or more of the microstructured chambers 15 in the box 1.

This microsystem 150 can be the object of numerous embodiments, but adapts advantageously to a 24-well plate such as illustrated in the figures by being constituted by twelve chambers 15. These chambers 15, having a microstructured surface, are of identical dimensions and are arranged so that there are two per row, each particularly preferably taking up a bioreactor in accordance with patent FR0954288, though without being limited thereto. The invention is not however limited to this architecture, and it is necessary to have at least one well per chamber only. For example, in another embodiment, a box according to the invention can comprise six microstructured chambers and a six-well plate.

Figure 5:
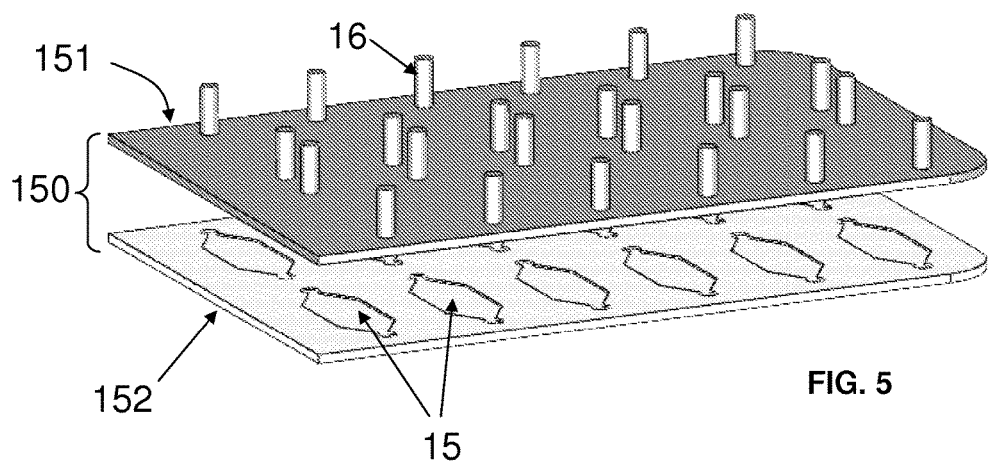
FIG. 5 is an exploded perspective view of the microsystem of the box according to the invention.

Two visible pieces in FIG. 5 can compose the microsystem 150: a lower plate 152 bearing the impression of the bottom of the chambers 15, and an upper plate 151.

Once these two plates are assembled hermetically, the cavities which appear are the chambers 15. These are small volumes in which the cells will develop in highly favourable conditions. In fact, the microstructures form complex channels offering a large contact surface with the fluid.

The presence of a microsystem 150 is nevertheless optional, with other structures able to house a chamber 15 of cellular culture being known to the person skilled in the art.

Embodiments of the Upper Plate of the Microsystem

The upper plate 151 can be the object of two advantageous embodiments. It is evident that the invention is limited neither to one nor the other of these embodiments, the upper plate 151 being an optional element. However, each of these two embodiments combines perfectly with all the characteristics described previously.

A material, PolyDiMethylSiloxane (PDMS), is particularly suitable for any one or other of these embodiments, as well as to the rest of the microsystem 150. In fact, it is transparent, porous to oxygen and to gases in general, and highly adapted to microstructuring, including its interest for cellular culture. In addition, it is easily deformable.

In the first embodiment, the upper plate 151 comprises sets of inlet and outlet connectors 16 of the microsystem 150, visible in most of the figures and particularly in FIG. 5. These sets of connectors 16 are of small tubes which are inserted into the holes 11 of the wells 10, and ensure fluidic communication in normal operation. If the wells 10 are wells of a multi-well plate 110, sealing can be optionally reinforced for example by a joint made of silicon material cast at the bottom of each well 10.

If the material which composes the sets of connectors 16 is supple, as is the case for silicon materials, these sets of connectors 16 will be able to accept the point of a pipette 2 by elasticity, used as an insemination tool. In fact, a pipette is a classic sampling and transfer instrument of a precise quantity of fluid, generally by suction due to a sort of pump called a propipette surmounting the latter. The term micropipette is used to designate a precision system preferably used in the invention, in which the pneumatic mechanism is integrated. In such a system, only the point (which is a disposable cone) is in contact with the fluid, but it would be incorrect to mention a pipette of generic type as being the fluid receptacle throughout the description.

The pipette 2, or more precisely the point of the pipette 2, can therefore be filled with liquid of cellular insemination. Now inserted in a set of connections 16, the point of the pipette 2 has its end at the base of the upper plate 151, that is, at the level of the ceiling of one of the chambers 15. Direct access to the interior of the chamber is permitted. Also, because of the tension due to the conical deformation of the set of connectors 16, sealing between the set of connectors 16 and the point of the pipette 2 inserted is ensured. A piston allows an operator to empty the column of liquid from the pipette by compression. The ejected volume can be controlled very precisely, in particular if the pipette being used is a micropipette. Since it is injected directly to the ceiling of the microstructured chambers, the fluid touches no other element than this chamber which it pervades. The fluid initially present, which can be for example culture medium or saline solution, is chased by buoyancy and escapes via another set of connectors 16 from the chamber. Because of these sets of connectors 16, optimal insemination is possible.

The architecture illustrated in the diagrams shows such a set of connectors 16 at inlet and outlet of each chamber 15, the sets of central connectors being fluid inlets, and the lateral ones being fluid outlets by analogy with the arrangement of the wells 10. It is evident that even if there are preferably two sets of connectors 16 per chamber, it suffices that a single one of these sets of connectors is connected as previously described to a well to allow direct cellular insemination. The sets of connectors of inlet and outlet can also be used variously. It is evident also that these sets of connectors allow the wells 10 and especially those outlet wells to be closest to the chambers. Metabolites optionally liberated by the cells during their exposure to a xenobiotic could be sampled immediately at their outlet of the chamber, leading to much more reliable results as they are non-biased by the phenomena of adsorption due to the length of the pipes.

Figure 6:
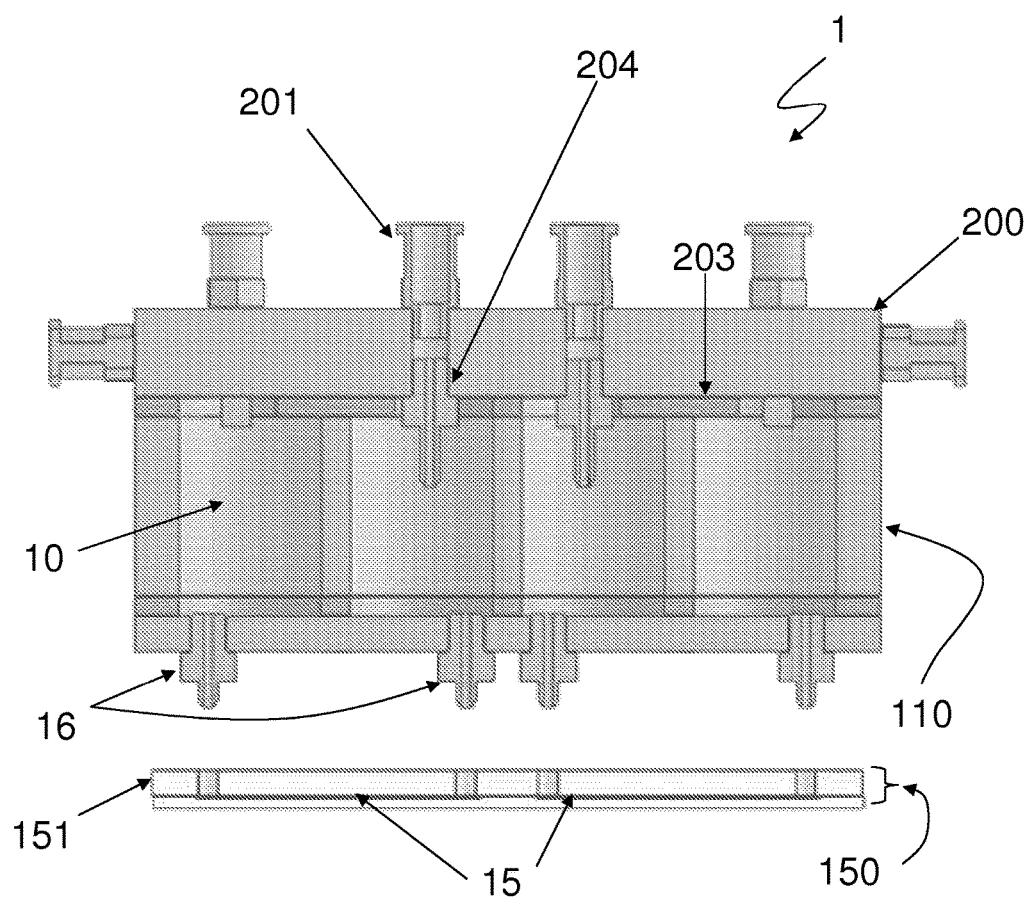
FIG. 6 is a transversal section of another possible embodiment of the lower casing of the box according to the invention, in which the microsystem is detachable.

In the second embodiment, illustrated in FIG. 6, as previously the box 1 comprises a microsystem 150 and at least one set of interface connectors 16 of the microsystem 150, but this time at least one microstructured chamber 15 is connected fluidically at inlet and/or at outlet by a set of connections 16 inserted detachably into a hole of the upper plate 151.

In other terms, the upper plate 151 is provided with holes in place of sets of connectors 16 of the first embodiment. These are no longer integrated into the microsystem 150, but are solid with the rest of the box 1. The sets of connectors 16 are preferably hard connectors, fixed in the holes 11 of the wells 10, for example by screwing, but also by adhesion, moulding, or any other known technique. These connectors 16 always perfuse the microstructured chamber 15, but are inserted detachably in the holes (they are for example driven in by force using the elasticity of the material, especially silicon, which makes up the plate 151) so that the microsystem 150 can easily be dismantled from the rest of the box 1. This dismantling offers numerous possibilities for study: fluorescent markings, activity tests, detachment and cellular counting. The material of the sets of connectors 16 is preferably polycarbonate or polypropylene.

The suppleness of PDMS is very important for the plate 151. By adjusting the diameter of the holes by elasticity, a hermetic junction between the microsystem and the connectors 16 is possible, as mentioned previously. This enables operation without risk of leakage, even after successive dismantling and reassembly of the microsystem 150.

Observation by Microscope of Cells During Culture

Because of their materials, the hood 200 and the microsystem 150 are autoclavable: according to the needs of users, it is possible in some cases to reutilise them for fresh culture after they have been cleaned and sterilised. Numerous materials exist for the multi-well plate 110. It is possible to first select a plate made of Polystyrene, as that in FIG. 7a. A plate 110 made of this material is for single use only and must be thrown away on completion of culture. It is actually inexpensive and completely transparent, making it easy to observe the cells during culture: since the bulk of the total multi-reactor box according to the invention is not as large as that of a Petri box, it can be placed fully under a microscope. It is actually preferable to be able to monitor the cells without perturbing them any time, both to ensure proper growth and to observe the direct toxicological impact of a substance.

Alternatively, a plate 110 made of Polycarbonate can be selected, that is, the same material as the hood 200. The ensemble is autoclavable, but Polycarbonate has the drawback of becoming opaque when it is machined, which is problematic for observing parts of the chamber under the well. An initial solution, if a multi-well plate 110 made of Polycarbonate is selected, such as that illustrated in FIG. 7b, consists of cutting out the bottom of the wells 10 and interposing between the box 110 and the microsystem 150 an additional fine plate 111 of polycarbonate and a PDMS joint ensuring sealing identical to that between the casing 100 and the hood 200. Clamping means similar to the means 20 then keeps the lower casing together. Because of this additional plate 111, completely transparent when not machined, observation by microscope is perfect and at the same time the ensemble is autoclavable.

Figures 7A, 7B, 7C:
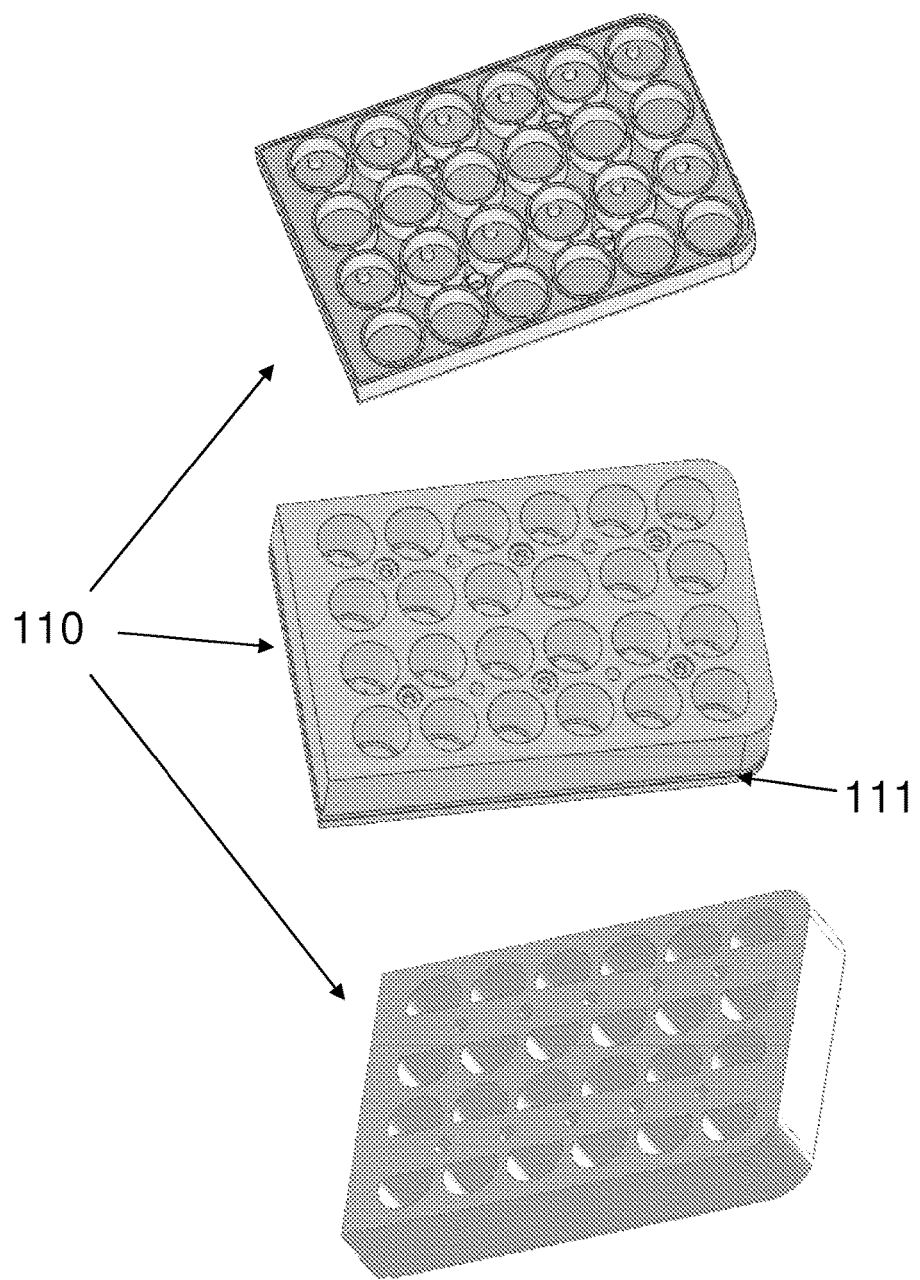
FIGS. 7a-7c illustrate three possible types of a multi-well plate usable in various embodiments of the box according to the invention.

A second solution, more gimmicky, consists of selecting a plate 110 with half-moon wells, illustrated in FIG. 7c. In fact, for example in FIG. 5 it is noted that the most interesting observation zone is the central part of the chambers 15. In fact, this is the very core of the cellular culture, the lateral parts of a chamber 15 being rather distribution channels for fluid. And this central zone is not located under the well 10, but between a well 10a and a well 10b, as is particularly evident in FIG. 2a or 2b. In the case of a half-moon box this is a disengaged rectangular zone which corresponds to the "flat" of the half-moon wells. A plate with half-moon wells is therefore well adapted to observation without the need to modify the bottom of the wells.

Figure 8A:
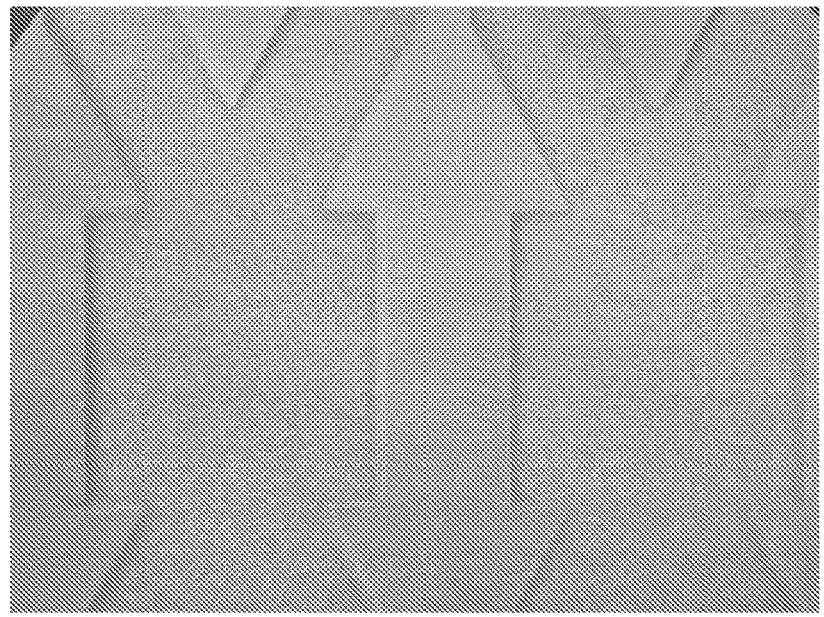
FIGS. 8a-8b are examples of microscope observations of cells in culture in various embodiments of the box according to the invention.

The images obtained from observing the cells through the entire multi-bioreactor box are remarkable in their precision, despite the thickness of the plastic. FIG. 8a is an example of this, precision of tens of microns is achieved, largely sufficient for verifying the presence of cells, their number, their homogeneity, etc. It is nevertheless possible to attain greater optical precision in the case of box with detachable microsystem 150 (FIG. 6) described previously, which especially allows morphological verification of cells.

During cellular culture, it suffices to halt circulation of fluid, and to dismantle the bioreactors of the casing 100 by pulling gently on the PDMS microsystem 150. It is feasible, as mentioned previously, to have a microsystem 150 constituted by several elements, each element able to comprise one chamber 15 only. When one chamber 15 in particular is to be observed, only that part of the microsystem 150 containing it is dismantled, and the circulation can be allowed to flow for the remainder.

Figure 8B:
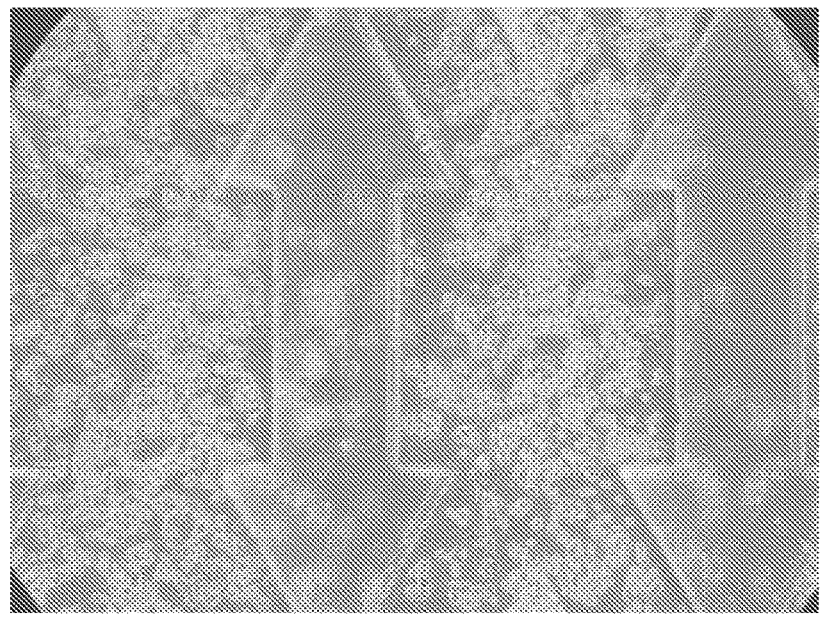

The microsystem 150 (or the microsystem element) can be introduced to a transparent sterile container and observed with an unequalled level of detail and contrast, since vision is direct, through a few millimeters of plastic only. The very interior of the cells can be observed, as shown in FIG. 8b, for example for extensively analysing certain effects of a tested substance. During the dismantling phase, the wells 10 connected to the microsystem 150 are emptied: with circulation discontinued, the fluid can be held in the fine channels of the screwed connectors 16 by simple capillarity. The microsystem 150 is then reconnected to the rest of the box 1 via the connectors 16 to continue and resume perfusion. It has been tested experimentally that it suffices to place a drop of culture medium in each inlet and outlet hole of the chambers 15 prior to reconnecting the assembly to avoid the risk of introducing an air bubble into a chamber 15.

Dynamic Cellular Culture System

According to another aspect, the invention relates to a dynamic cellular culture system comprising a box 1 according to the first aspect of the invention, at least one fluid circuit 300 and a pump 320, preferably a peristaltic pump, or any other means of fluid circulation known to the person skilled in the art. The different elements are connected to the circuit 300 by piping 310 constituted by tubes, preferably the shortest tubes possible, and to the internal surface the least adsorbent possible so as to limit any variation in concentration of a substance injected into the circuit 300.

The fact that the culture is dynamic signifies that there is recirculation in closed circuit of the fluid. In such a configuration the conditions for developing the cells are the closest to those of the organism as in prior art systems in which the fluid is either static, or never effects complete circuit rotation (movement in both directions of fluid in a chamber, which in particular disallows comparison between the fluid at the chamber inlet and that leaving the chamber, or single passage of the chamber by a fluid which is not reused).

Figure 10:
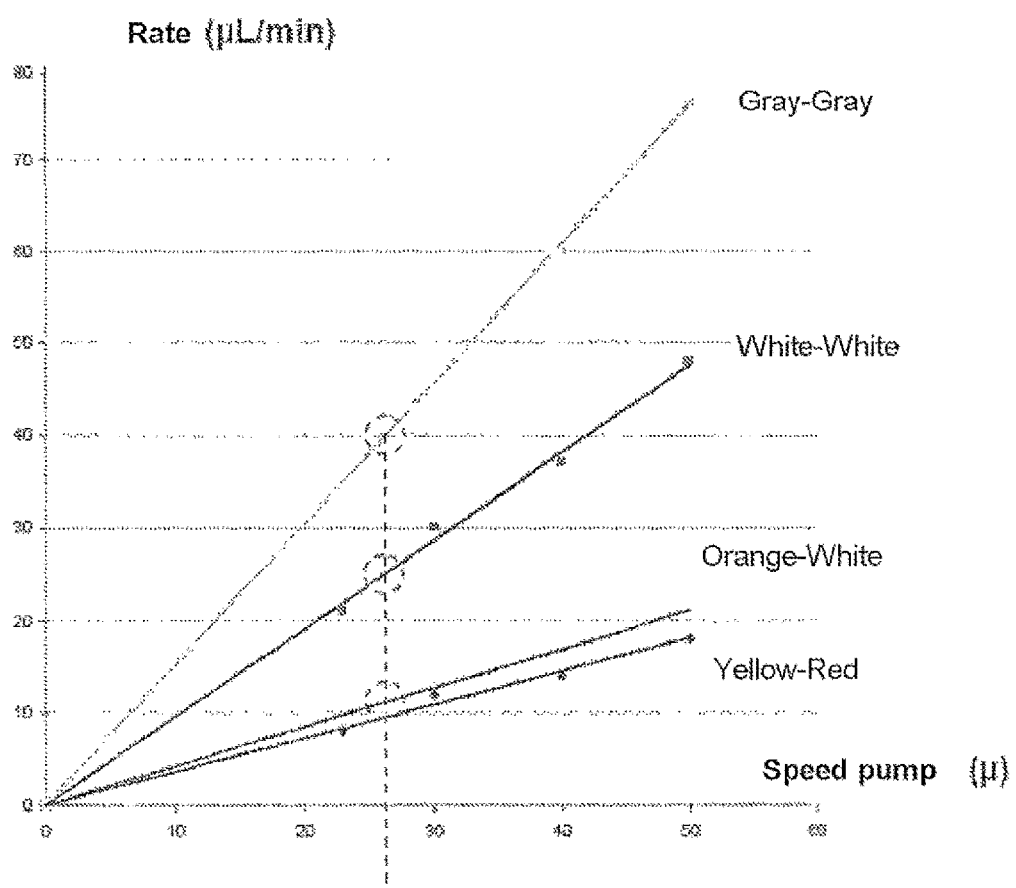
FIG. 10 is a graphic illustrating the fluid throughput obtained during experiments as a function of the operating speed of the pump for different pipe calibres.

A peristaltic pump is a pump in which fluid is entrained by compression and deformation of a tube, similarly to muscular contractions around the œsophagus, for example. This system is adapted for numerous reasons, in particular for application to cellular culture. First of all, it applies mainly to low throughput, for which there is high precision and considerable suppleness. Stopping the pump coincides exactly with immobilisation of the fluid in the circuit. Next, there are no elements other than the flexible tube in contact with the fluid. There is consequently no risk of contamination or leakage. Finally, a single pump can manage several fluid circuits at once, especially 24 for a particularly preferred Ismatec® IPC-N pump. This corresponds to all the chambers of two multi-reactor boxes, as described previously. By adjusting the internal diameter of the pipes 310 it is also possible to work at the same time with different rates according to the circuits, which for example can be useful for comparing different exposure kinetics to a substance. Tests have shown for example that it was possible to have simultaneous rates with a single peristaltic pump of 11, 25 and 40 μL/min simultaneously on three channels by using various calibres of standard pipes, identified by a colour code. FIG. 10 uses a graphic to illustrate the rates obtained as a function of the operating speed of the pump for four pipe calibres. The particularly preferred point of operation mentioned previously is set on the graphic.

Figure 9:
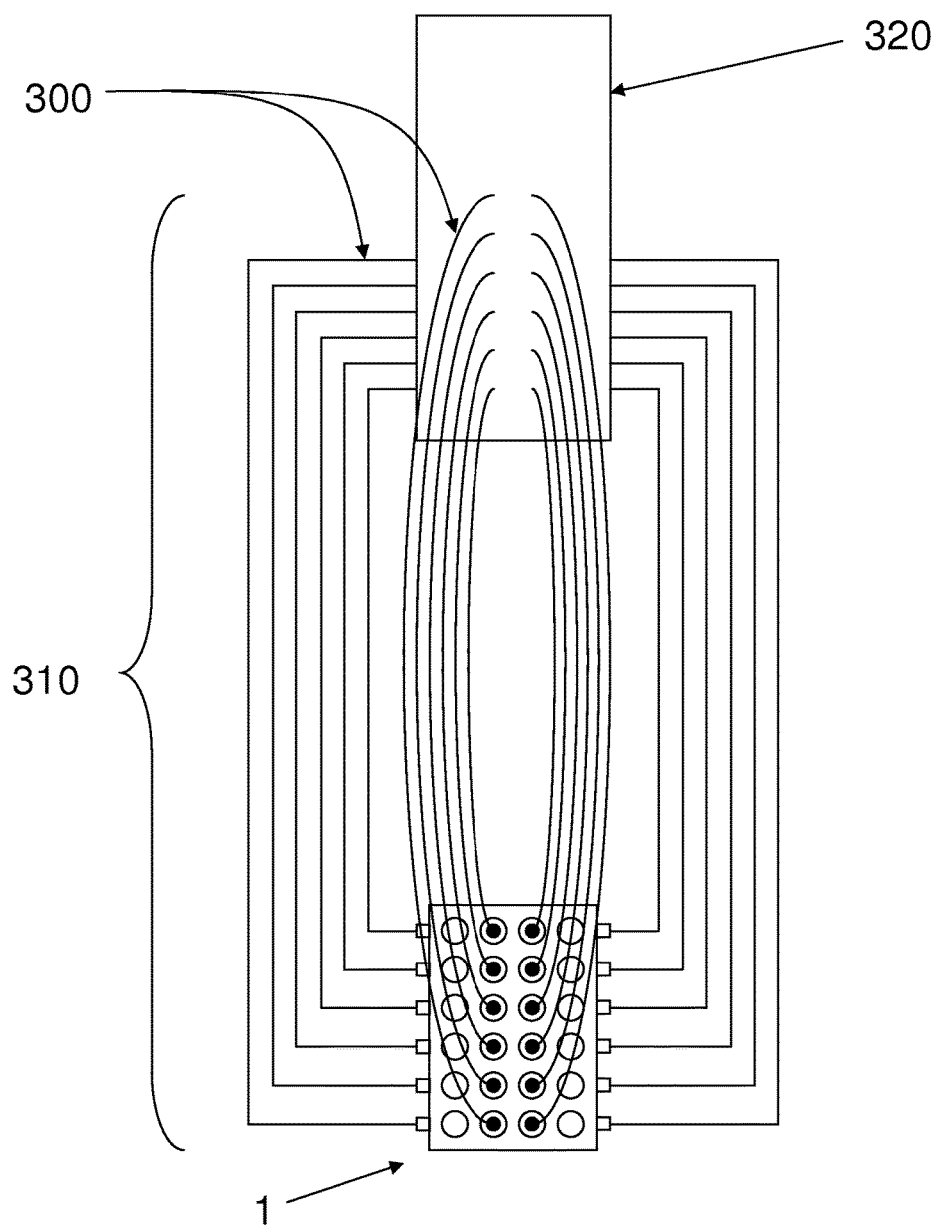
FIG. 9 is a diagram of a dynamic cellular culture system according to the other aspect of the invention.

An example of a circuit with a 12-channel pump 320 and a box 1 according to the invention is illustrated in FIG. 9. There is one fluid circuit 300 per chamber 15. It is evident that no additional element such as a tank or a bubble trap is required. The length of each circuit 300 and therefore the variations in concentration of injected substances are minimal. Also, each circuit advantageously has its sampling port 22, and can therefore be tested independently.

In this example, all the cultures are parallelised. Because of the sets of connectors 201 it is nevertheless possible to come up with highly varied architectures, with different bioreactors in series or in parallel. This modular aspect possible because of the dynamic aspect of the cellular culture of the system according to the invention simulates complex metabolisms, for example chaining of several bioartificial elements and/or of different types of cells characteristic of the same element. This is what is called co-culture. In fact, the metabolic response to a substance could be on several levels: not affecting a first element but affecting a second, causing secretion of a substance via a first element which could have repercussions on a second, etc. In a particularly preferred embodiment, each chamber 15 of the multi-reactor box simulates a different element (liver, kidney, pancreas . . . ), these bioartificial elements being cabled according to multiple circuits most closely representing the human architecture (kidney downstream of the liver, for example).

Membrane Inserts

Even more advantageously, the box according to the invention simulates some "filters" present in the organism. Accordingly, the haemato-encephalic barrier is an anatomical barrier which filters and controls the passage of blood substances and prevents them from passing freely from blood to extra-cellular liquid of the central nervous system. It isolates the grey substance from the rest of the organism and lets it have a specific medium. Only 2% of molecules lass through it freely. Substances which would prove neurotoxic if injected directly without the brain could prove to be completely safe if injected normally.

To take this into consideration it is possible to place membrane inserts into the well. These supports sold commercially are in the form of a small disc having the physico-chemical properties of the anatomical membrane to be simulated, and are installed in the inlet and outlet well 10 of the element to be isolated. The dynamic culture offered by the system according to the invention is again necessary to use this possibility. The structure described previously can be completed for example by simulating the passage in the blood of a molecule ingested by intestinal synthesis mucous.

Method of Cellular Insemination

According to yet another aspect, the invention relates to a method of cellular insemination of the multi-bioreactor box. As has been explained, the sets of connectors 16 can receive the point of a pipette 2.

Prior to performing insemination as such, it is necessary to access the sets of connectors 16 by opening the hood 200, generally after unscrewing the gripping means 20. Therefore, the bottom of the wells 10, and therefore the sets of connectors 16, are accessible. The operator uses a pipette 2 as insemination instrument.

Figure 2C:
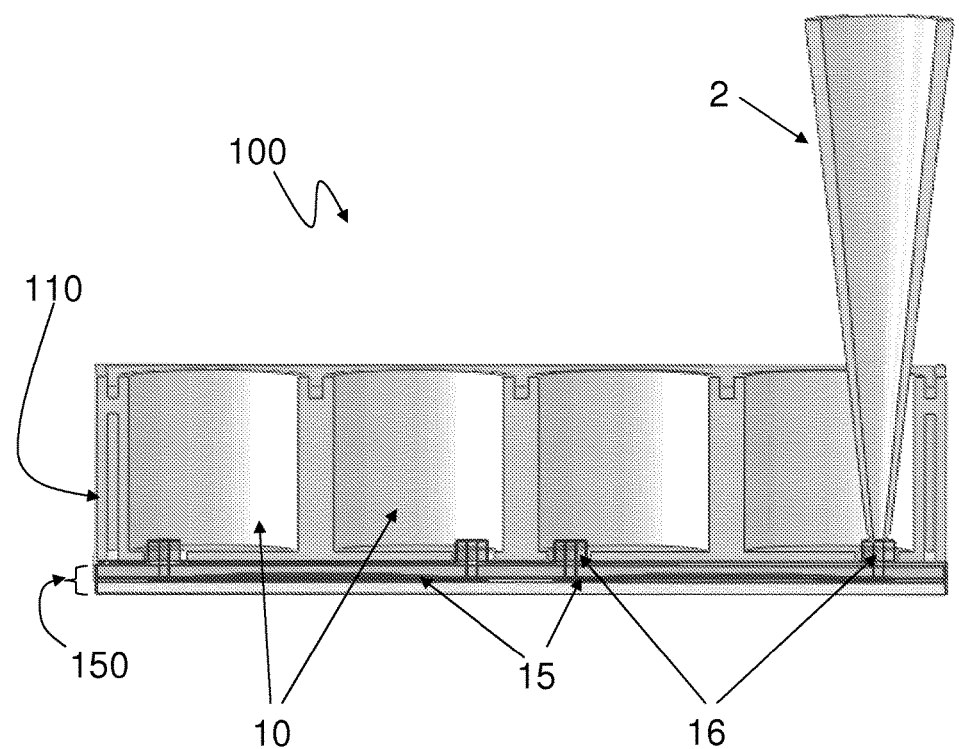

The insemination configuration is evident in FIG. 2c. Once each chamber is inseminated, it remains only to reclose the hood, connect the circuit or circuits 300, and trigger perfusion by the nutritive fluid to initiate development of the cells.

As is preferred, the pipette 2 is a gauged micropipette. As opposed to graduated pipettes, these pipettes are designed to contain a particular volume, for which they are extremely precise. Since the volume of a chamber 15 is known, as is the quantity of cells to be injected, it is possible to determine the optimal volume corresponding to insemination of a chamber and to select a well adapted gauged micropipette.

With such an instrument, the operator no longer has to repeat the following steps for each of the chambers: filling of the pipette 2, introducing its point to a set of connections 16 of the chamber, injecting the contents, and withdrawing the point. Each insemination takes a few seconds only, uses a well known and minimal quantity of cellular liquid, and guarantees optimal culture conditions.

As is particularly preferred, a multichannel pipette adapted to the dimensions of the multi-well plate 110 will be used. This is a pipette comprising a single sleeve, but of multiple points (in this case six in the case of a 24-well box as illustrated in the figures). This instrument simultaneously inseminates one chamber from each row, and therefore inseminates the whole box in only two manipulations.

A multichannel pipette can even be fitted on an automated distribution system. Such a system comprises a robotised arm and a supply or a fluid tank. It is moved on its own from one position to another to automatically inseminate all the chambers of a multi-bioreactor box, or even several. This type of device opens the way to a mass culture of bioartificial elements.

The invention claimed is:

1. A box (1) comprising a microsystem (150), a multi-well plate (110), and at least one set of interface connectors (16), the microsystem (150) comprising a lower plate (152) bearing the impression of at least one microstructured chamber of dynamic cellular culture (15), and an upper plate (151), wherein the at least one set of interface connectors (16) are fixed in holes (11) of the multi-well plate (110) at one end, wherein the at least one microstructured chamber of dynamic cellular culture (15) is connected fluidically at an inlet and/or at an outlet by the at least one set of interface connectors (16) inserted detachably in holes of the upper plate (151) at the other end, and wherein the holes of the upper plate (151) and the connectors (16) have matching diameters so as to provide a hermetic junction between the microsystem (150) and the connectors (16).

2. The box as claimed in the preceding claim, wherein said box further comprises at least one well (10), the hole (11) is the hole of the at least one well (10), and the microstructured chamber of dynamic cellular culture (15) is connected to said well (10) via one set of the at least one set of interface connectors (16).

3. The box as claimed in the preceding claim, wherein the bottom of the well (10) is at an altitude higher than any point of the microstructured chamber of dynamic cellular culture (15).

4. The box as claimed in the preceding claim, wherein the one set of interface connectors (16) is fixed to the hole (11) at the bottom of the well (10).

5. The box as claimed in claim 2 wherein each of said microstructured chamber of dynamic cellular culture (15) is connected to an inlet well (10a) and an outlet well (10b), and wherein said inlet well (10a) is perfused by a set of inlet connectors (16), and wherein said outlet well (10b) is perfused by a set of outlet connectors (16).

6. The box as claimed in the preceding claim, wherein said box comprises a lower casing (100) covered by a sealed hood (200) held by gripping means (20).

7. The box as claimed in the preceding claim, wherein the lower casing (100) comprises the microsystem (150) and the multi-well plate (110).

8. The box as claimed in the preceding claim, wherein the multi-well plate (110) is a disposable plate made of polystyrene.

9. The box as claimed in claim 7, wherein the multi-well plate (110) is an autoclavable plate made of polycarbonate.

10. The box as claimed in claim 6 wherein the sealed hood (200) comprises sets of male connectors (204) perfusing the well (10) and sets of female inlet connectors (201).

11. The box as claimed in the preceding claim, wherein said box comprises a male connector (204) and a female connector (201a) per inlet well (10a) and a male connector (204) and two female connectors (201b-c) per outlet well (10b).

12. The box as claimed in claim 1, wherein the microsystem (150) comprises polydimethylsiloxane.

13. The box as claimed in claim 2 wherein a membrane insert is arranged in at least one of the wells (10).

14. A dynamic cellular culture system, comprising
a box (1) as claimed in claim 1, and
at least one fluid circuit (300) comprising circulation piping (310) fitted with circulation means (320) and connected to at least one of said microstructured chamber of dynamic cellular culture (15).

15. The dynamic cellular culture system as claimed in the preceding claim, wherein the circulation means (320) is a multichannel peristaltic pump.

* * * * *